United States Patent [19]

Magruder et al.

[11] Patent Number: 4,723,957
[45] Date of Patent: Feb. 9, 1988

[54] SYSTEM FOR DELIVERING DRUG WITH ENHANCED BIOACCEPTABILITY

[75] Inventors: Paul R. Magruder, Palo Alto; Patrick S. L. Wong, Hayward; Felix Theeuwes, Los Altos; George V. Guittard, Cupertino, all of Calif.

[73] Assignee: Alza Corp., Palo Alto, Calif.

[21] Appl. No.: 827,027

[22] Filed: Feb. 7, 1986

[51] Int. Cl.$^4$ ............................................. A61K 9/22
[52] U.S. Cl. ...................................... 424/78; 424/487
[58] Field of Search .................. 604/890–897; 427/3; 526/93; 525/426; 424/78, 80

[56] References Cited

U.S. PATENT DOCUMENTS

| | | | |
|---|---|---|---|
| 4,224,427 | 9/1980 | Mueller et al. | 525/426 |
| 4,235,236 | 11/1980 | Theeuwes | 604/892 |
| 4,285,987 | 8/1981 | Ayer et al. | 427/3 |
| 4,320,759 | 3/1982 | Theeuwes | 604/892 |
| 4,327,725 | 5/1982 | Cortese et al. | 604/893 |
| 4,434,153 | 2/1984 | Urquhart et al. | 604/892 |
| 4,449,983 | 5/1984 | Cortese et al. | 604/892 |
| 4,474,751 | 10/1984 | Haslam et al. | 424/78 |
| 4,519,801 | 5/1985 | Edgren | 604/892 |
| 4,593,053 | 6/1986 | Jeune et al. | 424/80 |
| 4,608,048 | 8/1986 | Cortese et al. | 604/896 |

Primary Examiner—John D. Yasko
Assistant Examiner—Gene B. Kartchner
Attorney, Agent, or Firm—Paul L. Sabatine

[57] ABSTRACT

A composition of matter comprising a drug, a neutral hydrogel and an ionic hydrogel. The composition can be administered from a delivery system to a biological receptor over time.

2 Claims, 6 Drawing Figures

SYSTEM FOR DELIVERING DRUG WITH ENHANCED BIOACCEPTABILITY

FIELD OF THE INVENTION

This invention pertains to a delivery system for delivering a drug with enhanced bioacceptability. More particularly, the invention concerns a delivery system for delivering a drug with a concomitant lessening of the incidence of adverse effects of the drug on the biological environment. The invention relates also to a composition of matter comprising a drug, and to a method for using the dispensing system.

BACKGROUND OF THE INVENTION

There are many beneficial drugs known to medicine, veterinary and pharmacy that are administered for producing a beneficial effect that often have a serious shortcoming associated with their use. For example, the electrolyte drug potassium chloride is the pharmaceutically acceptable salt most frequently used when the benefit of the potassium cation is desired for its indicated therapeutic effect. Potassium chloride is used when hypokalemia exists, as a treatment with certain diuretics, in steroid therapy, and for relieving the symptoms associated with Menier's disease. However, serious shortcomings are associated with its use, mainly potassium chloride is an irritant of gastrointestinal mucosa, and its use often leads to bowel lesions. Another important drug that possesses similar shortcomings is aspirin. Aspirin, or acetylsalicylic acid, is used widely as an antipyretic and as an analgesic in a variety of medical conditions. Aspirin is a very valuable drug; however, the use of this drug in conventional dosage forms often is accompanied by gastrointestinal irritation. Another drug whose usefulness is compromised by unwanted effects is indomethacin. Indomethacin exhibits both analgesic and anti-inflammatory properties and it is used mostly for the treatment of rheumatoid arthritis. The most frequent unwanted actions associated with dosage forms containing this drug are gastrointestinal mucosal disturbances similar to those mentioned immediately above.

Other drugs, such as the nonsteroidal, anti-inflammatory, pharmaceutically acceptable salts of ibuprofen, diclofenac, naproxen, fenoprofen, and the like are widely used for the treatment of inflammatory conditions, but they also suffer from the disadvantage that they can cause irritation of the mucosal lining of the digestive tract. Then, too, the widely used antiscurvy vitamin, ascorbic acid, is known to elicit a similar irritation in warm-blooded animals, including humans. In many instances the irritation occurs as a result of an irritant producing drug being presented in a concentrated dosage form directly to the lining of the digestive tract, prior to diluting the drug with digestive fluids.

The prior art has provided novel therapeutic systems manufactured in the form of osmotic devices for the precision administration of drugs at controlled delivery patterns over extended operational delivery times. These unique systems are disclosed in U.S. Pat. Nos. 3,845,770 and 3,916,899, both issued to patentees Theeuwes and Higuchi. The systems disclosed in these patents comprise a semipermeable wall that surrounds a compartment containing a drug that is dispensed through at least one exit passageway in the wall. The dispensing system disclosed by Theeuwes and Highuchi represent an outstanding and pioneering advancement in the delivery art, and they are extraordinarily effective for delivering all kinds of drugs in the form of saturated solutions. While these systems are useful for dispensing innumerable drugs to a biological environment of use, there is an occasional instance where an unexpected advancement is needed in these systems for dispensing potentially irritating drugs of the type mentioned above. Thus, in light of this presentation, it will be appreciated by those versed in the dispensing art that if a practical system is made available for dispensing such beneficial drugs, with a lessening of unwanted effects, such a dispensing system would have a definite use and represent a valuable contribution to medicine, veterinary and the pharmaceutical arts.

OBJECTS OF THE INVENTION

Accordingly, in view of the above presentation, it is an immediate object of this invention to provide a delivery system, a composition of matter, and a method for the controlled delivery of a drug, and which system, composition and method represent an unexpected improvement in the dispensing art and substantially overcome the disadvantages known to the prior art.

Another object of the invention is to provide a delivery system for delivering a beneficial drug that is prone to exhibit adverse effects which are attenuated by using the delivery system of this invention for delivering it to a biological environment of use.

Another object of the invention is to provide a delivery system for administering a drug accompanied by a lessening of mucosal tissue irritation.

Another object of the invention is to provide a delivery system for administering a drug in a concentrated amount that is presented in less than a concentrated amount to a drug receiving biological surface of the environment of use.

Another object of the present invention is to provide an improvement in drug delivery by making available a delivery system for the rate controlled and continuous delivery of a beneficial drug in means for presenting the drug in a diluted amount to the environment of use.

Another object of the present invention is to provide a drug delivery device for the administration of a drug comprising means for lessening its direct contact with the tissues of the gastrointestinal tract for correspondingly decreasing the drug's ability to produce tissue injury, while concomitantly administering the drug in a therapeutically effective dosage amount.

Another object of the invention is to provide a dispensing device comprising means for dispensing a drug for substantially preventing it from contacting directly the mucosal wall of the digestive tract where such contact is detrimental prior to its dilution with digestive fluid present in the gastrointestinal tract.

Another object of the invention is to provide a delivery device that enables the administration of drug in the gastrointestinal tract without permitting contact of undissolved drug with the lining of the gastrointestinal tract before its in vivo dilution with gastrointestinal fluid.

Another object of the present invention is to provide a dispensing device for delivering a beneficial drug comprising means for continuously diminishing the concentration of a drug presented to the gastrointestinal tract for topical and systemic use.

Other objects, features and advantages of the invention will be more apparent to those versed in the dispensing art from the following detailed specification taken in conjunction with the drawing figures and the accompanying claims.

BRIEF DESCRIPTION OF THE DRAWINGS

In the drawings, which are not drawn to scale, but are set forth to illustrate various embodiments of the invention, the drawing figures are as follows.

DETAILED DESCRIPTION OF THE DRAWINGS

Figure 1:
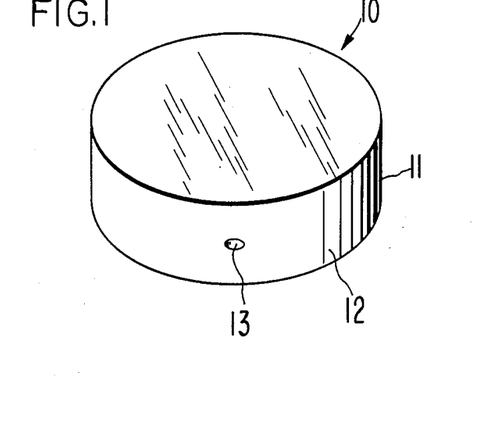
FIG. 1 is a view of a dispensing device designed for orally administering a beneficial drug to the gastrointestinal tract.

Turning now to the drawing figures in detail, which drawing figures are examples of delivery devices provided by the invention, and which drawing figures are not to be construed as limiting the invention, one example of a dispensing device is seen in FIG. 1 identified by the numeral 10. In FIG. 1, dispensing device 10 comprises a body means 11 comprising a wall means 12 for surrounding and forming an internal compartment, not seen in FIG. 1, and at least one exit means 13 for connecting the exterior of device 10 with the interior of device 10.

Figure 2:
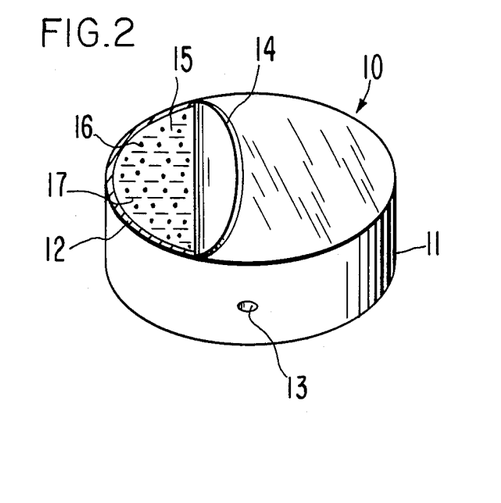
FIG. 2 is an opened view of the delivery system of FIG. 1 for illustrating the internal structure of the delivery system.

In FIG. 2, an osmotic dispensing device 10 is seen in opened view with wall 12 opened at 14. In FIG. 2, dispensing device 10 comprises body member 11, wall 12 and internal compartment 15. Wall 12 of device 10 comprises a nontoxic polymeric composition that is totally, or in at least a part, permeable to the passage of an external fluid, and it is substantially impermeable to the passage of a beneficial drug formulation 16 present in compartment 15. The polymeric composition comprising wall means 12 is inert and it maintains its physical and chemical integrity during the dispensing life of device 10. The phrase, "physical and chemical integrity" denotes wall means 12 does not lose its structure and it does not change during the dispensing life of device 10.

Internal compartment 15 houses a dispensable composition comprising a beneficial drug formulation 16, identified by dots, which drug formulation is releasably blended with a hydrogel carrier means 17, identified by dashes. Beneficial drug formulation 16 comprises a drug that can be from insoluble to very soluble in fluid that passes through wall means 12 into compartment 15. Beneficial drug formulation 16 in compartment 15 comprises, in a presently preferred embodiment, a drug that can irritate mucosal tissue, such as the mucosal tissues of the gastrointestinal tract. The drug causes irritation by directly contacting the mucosal tissues generally in a saturated amount and prior to the drug undergoing dissolution, dissolving or dilution by fluid present in an animal body, such as fluid present in the gastrointestinal tract. The hydrogel carrier is (1) a means for substantially lessening or substantially avoiding the incidence of irritation associated with a drug that produces irritation on tissue contact, (2) a means for substantially reducing the concentration of an irritating drug formulation dispensed by device 10 and presented to a mucosal receptor site, and (3) a means for substantially lessening direct drug mucosal contact and concomitantly lessening the degree of tissue irritation associated with an irritant drug.

Hydrogel carrier means 17 comprises a hydrophilic polymeric composition that is noncross-linked or lightly cross-linked and it possesses the ability to form a dispensable formulation by homogeneously or heterogeneously blending with drug formulation 16. Hydrogel carrier means 17 can optionally be described as a tissue contact reducing means as it reduces direct contact of device 10, and direct contact of drug formulation 16 with a mucosal tissue. In operation, hydrogel means absorbs and/or imbibes fluid, expands and forms a dispensable formulation that is released from device 10 simultaneously transporting drug formulation 16 therewith. On its release, carrier means 17 further expands in the presence of gastrointestinal fluid, thereby reducing direct drug contact of drug formulation 16 with the mucosal tissue. Drug formulation 16 on its controlled release from device 10 in the accompanyment of hydrogel means 17, undergoes dissolution in gastrointestinal fluid by formulation 16 mixing with fluid and forming a diluted suspension, or formulation 16 dissolves in gastrointestinal fluid and forms a solution. In either instance, the combined operations of the hydrogel means and the drug formulation fluid interactions, present a less irritating drug formulation to the mucosal tissue, thereby lessening the incidence of unwanted irritation.

Figure 3:
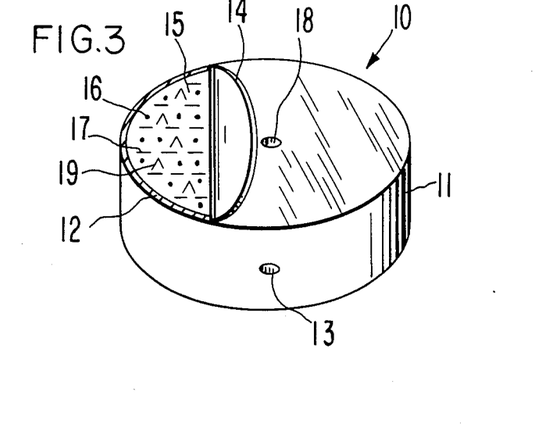
FIG. 3 is an opened view of the delivery system of FIG. 1 for illustrating the multiplicity of components housed in the compartment of the delivery system.

FIG. 3 illustrates another embodiment provided by the invention. In FIG. 3, dispensing device 10 is seen in opened section with wall 12 opened and peeled-back at 14. In FIG. 3, dispensing device 10 comprises body member 11, wall means 12, passageway means 13 in wall 12 and internal compartment 15. In FIG. 3, dispensing device 10 comprises more than one passageway as seen by the presence of second exit passageway 18. Internal compartment 15 houses a dispensable composition comprising a beneficial drug formulation 16, and a blend of at least two hydrogel means 17 and 19. The two hydrogel means both exhibit the ability to interact with fluid and swell to some equilibrium state. Hydrogel means 17 in a preferred embodiment comprises a neutral hydrogel that can swell and expand in the presence of both drug formulation 16 and fluid imbibed into compartment 15 for forming a dispensable carrier. The in situ formed carrier transports drug formulation 16 and second hydrogel 19 from compartment 15. The second hydrogel 19, in a preferred embodiment, comprises an ionic hydrogel that exhibits a smaller degree of swelling in the presence of drug formulation 16 and first hydrogel means 17 in compartment 15. In operation, on the concomitant release of drug formulation 16, first hydrogel means 17 and second hydrogel means 19 from compartment 15, both means 17 and means 19 interact with fluid in the gastrointestinal environment of use, swell and retain absorbed fluid within their respective hydrogel structural networks. Simultaneously drug formulation 16 released from compartment 15 undergoes further dissolution, or dissolving in fluid, thereby decreasing the concentration of the suspension or solution formed in the environment of use. Through these combined integrated, reciprocal actions, mainly, (1) by the expansion of hydrogel means 17 and 19, the contact of drug formulation with mucosal tissue is reduced by forming a hydrogel interface between drug formulation 16 and the in vivo tissue, and (2) by the dissolution or dissolving of the drug formulation in the fluid and in the presence of the expanding hydrogels, the concentration of drug is decreased in vivo, whereby the irritation of tissue is diminished over time.

Figure 4:
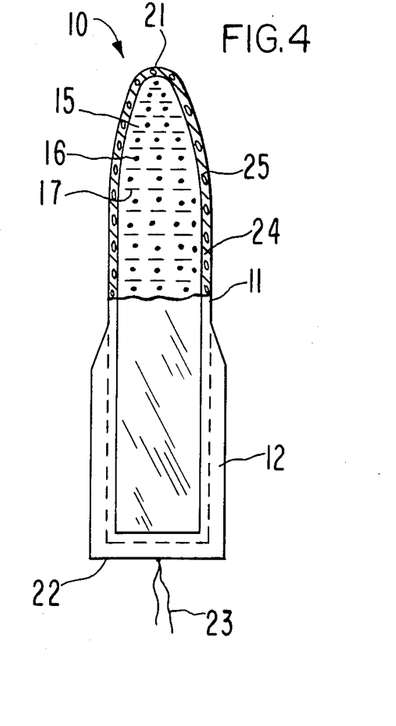
FIG. 4 is an opened view of a delivery system provided for dispensing a drug in a body passageway.

FIG. 4 illustrates another embodiment of dispensing device 10. In FIG. 4, dispensing device 10 is designed, sized and shaped for placement in an animal body passageway such as a vagina or the ano-rectal canal. Device 10 in the depicted embodiment, comprises an elongated cylindrical, self-sustaining shape with a rounded lead end 21, a trailing end 22, and a manually controlled string 23 for easily removing device 10 from a biological passageway. Device 10 of FIG. 4 is substantially identical with device 10 as described above and it operates in a like manner. Device 10 of FIG. 4 comprises body 11 and wall 12. Wall 12 comprises a semipermeable composition permeable to the passage of fluid and substantially impermeable to the passage of drug formulation 16. Wall 12 surrounds, in part, a microporous wall 24. Microporous wall 24 is formed of a microporous polymer composition comprising at least one or a plurality of pores 25. Micropores 25 are an exit means for releasing drug formulation 16 from device 10. In this capacity, a plurality of micropores 25 function as a diffuser and as an additional means for diffusing drug formulation 16 to the environment of use. Microporous releasing wall 24 thereby further lessens the incidence of irritation of the vaginal mucosal or ano-rectal mucosal tissues.

Figure 5:
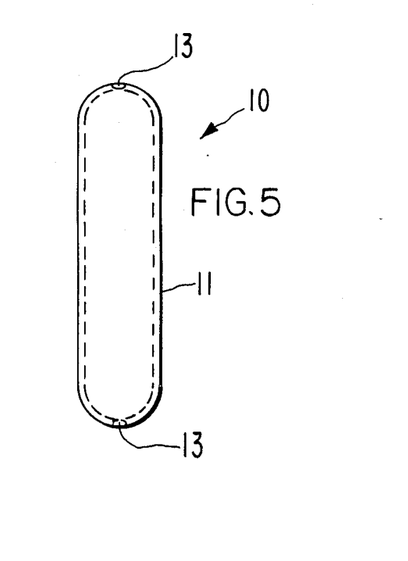
FIG. 5 is an opened view of a delivery system designed for use as a body implant.
Figure 6:
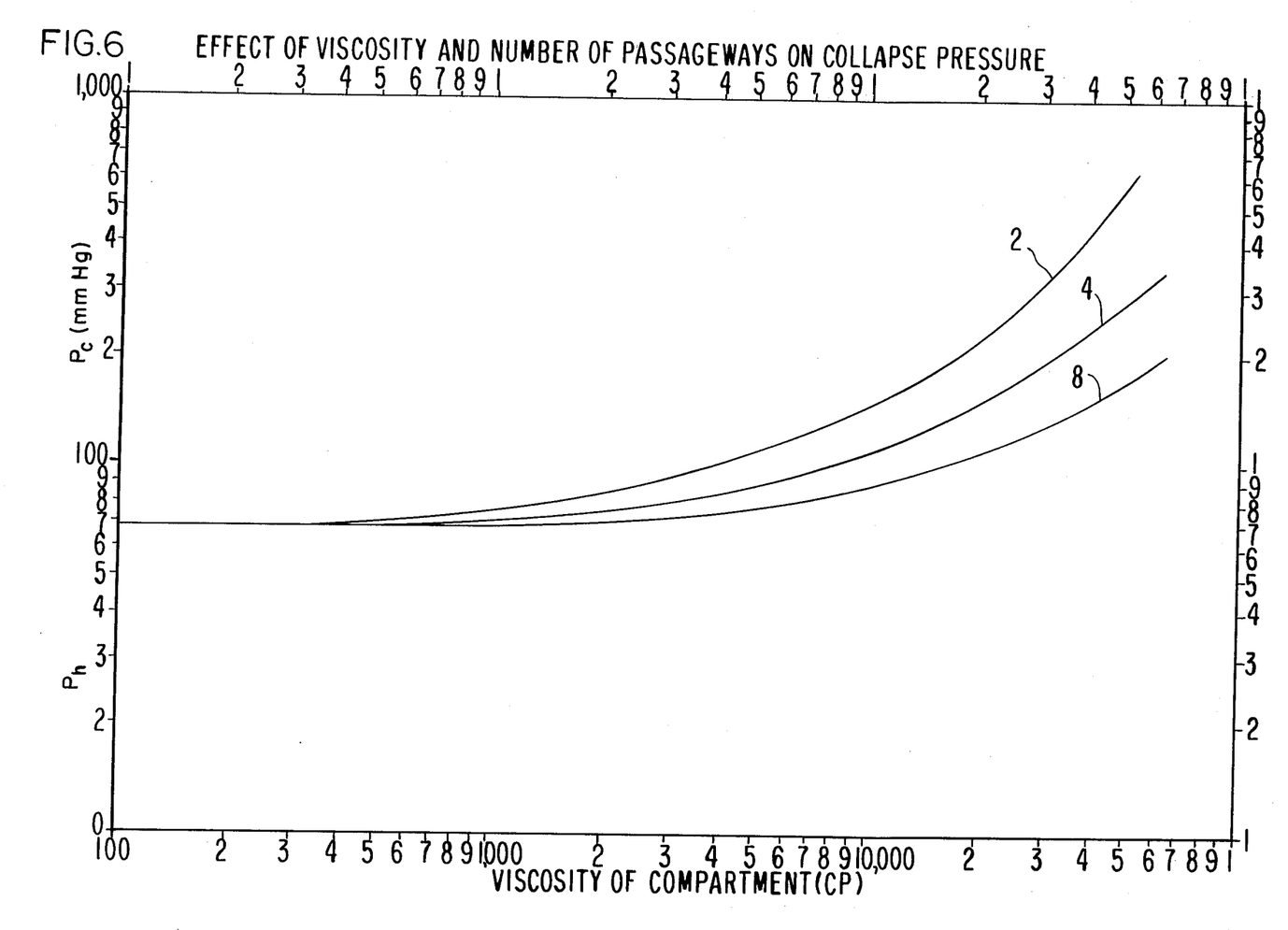
FIG. 6 is a graph indicating viscosity measurements in the compartment of a device.

FIG. 5 illustrates another device of the invention. FIG. 5 depicts an osmotic device 10 shaped and adapted for use as an implant. Implantable device 10 possesses the structural features and operates in the manner described above.

While FIGS. 1 through 5 are illustrative of dispensing devices that can be made according to the invention, it is to be understood these devices are not to be construed as limiting the invention, as the devices can take a wide variety of shapes, sizes and forms for delivering a beneficial drug to an environment of use. For example, the devices include buccal, artificial gland, cervical, intrauterine, nasal, subcutaneous, dermal, and the like. The devices can be adapted for administering a beneficial drug to animals, which term includes warm-blooded mammals, humans, primates, household animals, sport animals, farm animals and zoo animals. The devices can be adapted also for administering a drug in a therapeutically effective amount to avians, pisces and reptiles.

DETAILED DESCRIPTION OF THE INVENTION

In accordance with the practice of the invention, it has now been found that delivery device 10 can be manufactured with a wall formed of materials that do not adversely affect the beneficial drug formulation, the hydrogel means, the animal, or the like. Wall 12 comprises totally, or in at least a part, a polymeric composition permeable to the passage of an external aqueous-type fluid, such as water and a biological fluid, while remaining essentially impermeable to the passage of a beneficial drug formulation, hydrogels, and the like.

Typical materials for forming wall 12 comprise selectively semipermeable polymers known to the art as osmosis and reverse osmosis membranes. These polymeric compositions comprise a cellulose ester, cellulose ether, cellulose ester-ether, cellulose acylate, cellulose diacylate, cellulose triacylate, cellulose acetate, cellulose diacetate, cellulose triacetate, agar acetate, amylose triacetate, beta glucan acetate, cellulose acetaldehyde dimethyl acetae, cellulose acetate ethyl carbamate, cellulose acetate methyl carbamate, cellulose acetate succinate, cellulose acetae dimethylaminoacetate, cellulose acetate ethylcarbamate, cellulose acetate chloroacetate, cellulose dipalmate, cellulose dioctanoate, cellulose dicarpylate, cellulose dipentanlate, cellulose acetate valerate, cellulose acetate succinate, cellulose propionate succinate, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876; 3,276,586; 3,541,005; 3,541,006, and 3,546,142; semipermeable polymers as disclosed by Loeb and Sourirajan in U.S. Pat. No. 3,133,132; pH stable, lightly cross-linked, semipermeable polystyrene; non-mobile, cross-linked, semipermeable poly(sodium styrene sulfonate); semipermeable poly(vinylbenzyl-trimethyl-ammonium chloride); cellulose acetate having a degree of substitution up to 1 and an acetyl content up to 21%; cellulose diacetate having a degree of substitution of 1 to 2 and an acetyl content of 21 to 35%; cellulose triacetate having a degree of substitution of 2 to 3 and an acetyl content of 35 to 44.8%. Semipermeable polymers are known to the dispensing art in U.S. Pat. Nos. 3,845,770; 3,916,899; 4,160,020, and 4,250,108. Generally the semipermeable compositions used for wall 12 will have a fluid permeability of $10^{-3}$ to $10^{-1}$ (cc mil/cm$^2$ hr/atm) expressed per atmosphere of hydrostatic or osmotic pressure difference across wall 12 can be used for the intended purpose. The phrase, "non-mobile, cross-linked bond" is used in its conventional meaning to indicate the cross-linked bond is stable in the presence of acids and bases, it does not hydrolyze or break in these environments.

The microporous polymers used for forming wall 12, alone and in combination with a semipermeable polymer, are essentially inert, they maintain their physical and chemical integrity during the period of drug release, and they can generally be described as having a sponge-like appearance that provides supporting structure for microscopic-sized interconnected pores or voids. The materials can be isotropic wherein the structure is homogeneous throughout a cross-sectional area, or they can be anisotropic wherein the structure is non-homogeneous throughout a cross-sectional area. The pores can be continuous pores that have an opening on both faces of a microporous wall or a microporous lamina; pores interconnected through tortuous paths of regular and irregular shapes including curved, curved-linear, randomly oriented continuous pores; hindered connected pores and other porous paths discernible by microscopic examination. Generally microporous membranes are defined by the pore size, the number of pores, the tortuosity of the microporous path and the porosity which relates to the size and the number of pores. The pore size of a microporous membrane is easily ascertained by measuring the observed pore diameter at the surface of the material under the electron microscope. Generally materials possessing from 5% to 95% pores and having a pore size of from 10 angstroms to 100 microns can be used for making the device. The pore size and other parameters characterizing the microporous structure can be obtained from flow measurements, where a liquid flux, J, is produced by a pressure difference $\Delta P$ across the wall. The liquid flux through a lamina with pores of uniform radius extended through the membrane and perpendicular to its surface with area, A, is given by relation (1):

$$J = \frac{N\pi r^4 \Delta P}{8\eta \Delta x} \quad (1)$$

wherein J is the volume transported per unit time and membrane area containing N number of pores of radius r, $\eta$ is the viscosity of the liquid, and $\Delta P$ is the pressure difference across the membrane with a thickness $\Delta x$. For this type of membrane the number of pores N can be calculated from relation (2), wherein $\epsilon$ is the porosity defined as the ratio of void volume to total volume of the membrane, and A is the cross-sectional area of the membrane containing N pores:

$$N = \epsilon \times \frac{A}{\pi r^2} \quad (2)$$

The pore radius is calculated from relation (3):

$$r = \left( 8 \frac{\tau \cdot J \cdot \Delta x \cdot \eta}{A \cdot \Delta P \cdot \epsilon} \right)^{\frac{1}{2}} \quad (3)$$

wherein J is the volume flux through the membrane per unit area produced by the pressure difference $\Delta P$ across the membrane, $\eta$, $\epsilon$ and $\Delta x$ have the meaning defined above and $\tau$ is the tortuosity defined as the ratio of the diffusional path length in the membrane to the membrane thickness. Relations of the above type are discussed in *Transport Phenomina In Membranes* by N. Lakshminatayanaiah, Chapt. 6, 1969, published by Academic Press, Inc., NY.

As discussed in the above named reference, p 336, Table 6.13, the porosity of the lamina having pore radius, r, can be expressed relative to the size of the transported molecule having a radius, a, and as the ratio of molecule radius to pore radius, a/r, decreases, the membrane becomes porous with respect to this molecule. That is, when the ratio, a/r is less than 0.3, the membrane becomes substantially microporous as expressed by the osmotic reflection coefficient, $\sigma$, which decreases below 0.5. Microporous membranes with a reflection coefficient, $\sigma$, in the range of less than 1, usually from 0 to 0.5, and preferably less than 0.1 with respect to the active agent, are suitable for fabricating the system. The reflection coefficient is determined by shaping the material in the form of a membrane and carrying out water flux measurements as a function of the hydrostatic pressure difference and as a function of the osmotic pressure difference caused by the active drug. The osmotic pressure difference creates a hydrostatic volume flux, and the reflection coefficient is expressed by relation (4):

$$\sigma = \frac{\text{hydrostatic pressure difference} \times \text{osmotic volume flux}}{\text{osmotic pressure difference} \times \text{hydrostatic volume flux}} \quad (4)$$

Properties of microporous materials are described in *Science*, Vol. 170, pp 1302–05, 1970; *Nature*, Vol. 214, p 285, 1967; *Polymer Engineering and Science*, Vol. 11, pp 284–388, 1971; Industrial Processing With Membranes, by R. E. Lacy and Sidney Loeb, pp 131–34, 1972, published by Wiley Interscience, NY; and in U.S. Pat. Nos. 3,567,809 and 3,751,536.

Microporous materials having a preformed structure are commercially available and they can be made by art-known methods. The microporous materials can be made by etched nuclear tracking; by cooling a solution of flowable polymer below the freezing point whereby solvent evaporates from the solution in the form of crystals dispersed in the polymer and then using the polymer followed by removing the solvent crystals; by cold or hot stretching at low or high temperatures until pores are formed; by leaching from a polymer a soluble component by an appropriate solvent; by ion exchange reaction; and by polyelectrolyte processes. Processes for preparing microporous materials are described in *Synthetic Polymer Membranes*, by R. E. Kesting, Chapts. 4 and 5, 1971, published by McGraw Hill, Inc.; *Chemical Reviews*, "Ultrafilter Membrane and Ultrafiltration", Vol. 18, pp 373–455, 1934; *Polymer Eng. and Sci.*, Vol. 11, No. 4, pp 284–88, 1971; *J. Appl. Poly. Sci.*, Vol. 15, pp 811–29, 1971; and in U.S. Pat. Nos. 3,565,259; 3,615,024; 3,751,536; 3,801,692; 3,852,224; and 3,849,528.

Microporous materials useful for making the wall include microporous polycarbonates comprising linear polyesters of carbonic acid in which carbonate groups recur in the polymer chain; microporous materials prepared by the phosgenation of a dihydroxyl aromatic such as a bisphenol; microporous poly(vinylchloride); microporous polyamides such as poly(hexamethylene adepamide); microporous modacrylic copolymers including those formed from poly(vinylchloride) and (acrylonitrile); styrene-acrylic acid and its copolymers; porous polysulfones characterized by diphenylene sulfone groups in a linear chain thereof; halogenated poly(vinylidene); polychloroethers; acetal polymers; polyesters prepared by the esterification of a dicarboxylic acid or anhydride with an alkylene polyol; poly(alkylenesulfides); phenolic polyesters; microporous poly(saccharides); microporous poly(saccharides) having substituted and unsubstituted anhydroglucose units; asymmetric porous polymers; cross-linked olefin polymers; hydrophobic or hydrophilic microporous homopolymers; copolymers or interpolymers having a reduced bulk density; in materials described in U.S. Pat. Nos. 3,597,752; 3,643,178; 3,654,066; 3,709,774; 3,718,532; 3,803,061; 3,852,224; 3,853,631; and 3,852,388; in British Pat. No. 1,126,849 and in *Chem. Abst.*, Vol. 71, 4274F, 22572F and 22573F, 1969.

Additional microporous materials include poly(urethanes); cross-linked, chain-extended poly(urethanes); microporous poly(urethanes) as in U.S. Pat. No. 3,524,753; microporous poly(imides); microporous poly(benzimidazoles); collodion(cellulose nitrate with 11% nitrogen); regenerated proteins; semisolid, cross-linked poly(vinylpyrrolidone); microporous materials prepared by diffusion of multivalent cations into polyelectrolyte sols as in U.S. Pat. No. 3,565,259; anisotropic permeable microporous materials of ionically associated polyelectrolytes; porous polymers formed by the coprecipitation of a polycation and a polyanion as described in U.S. Pat. Nos. 3,276,589; 3,541,055; 3,541,066, and 3,546,142; derivatives of poly(styrene) such as poly(sodium styrene sulfonate) and poly(vinyl benzyltrimethyl ammonium chloride); the microporous materials described in U.S. Pat. Nos. 3,615,024; 3,646,178; and 3,852,224.

Further, the microporous forming materials used for the purpose of the invention include the embodiment wherein the microporous membrane is formed in situ by a pore-former being removed by dissolving or leaching it to form the microporous wall comprising pores of controlled porosity during the operation of the system. The pore-former can be a solid or a liquid. The term liquid, for this invention, embraces semi-solids and viscous fluids. The pore-formers can be inorganic or organic. The pore-formers suitable for the invention include pore-formers that can be extracted without any chemical change in the polymer. The pore-forming solids having a size of about 0.1 to 200 microns and they include alkali metals such as sodium chloride, sodium bromide, potassium chloride, potassium sulfate, potassium phosphate, sodium benzoate, sodium acetate, sodium citrate, potassium nitrate, and the like. The alkaline earth metal salts such as calcium phosphate, calcium nitrate, and the like. The transition metal salts such as ferric chloride, ferrous sulfate, zinc sulfate, cupris chloride, manganese fluoride, manganese fluorosilicate, and the like. The pore-formers include organic compounds such as polysaccharides, sucrose, glucose, fructose, mannitol, lactose, sorbitol, monosaccharides, disaccharides, and the like. Also, organic aliphatic and aromatic ols, including diols and polyols as exemplified by polyhydric alcohols, poly(alkylene glycols), polyglycols, alkylene glycols, poly($\alpha$-$\omega$)-alkylenediol esters or alkylene glycols and the like. The pore formers are nontoxic, and on their removal from the wall channels are formed through the wall that fill with fluid. The channels become a path that extend from one side of the wall to the other for letting a drug formulation leave the dispensing system. In a presently preferred embodiment the nontoxic pore-forming agents are selected from the group consisting of inorganic and organic salts, carbohydrates, poly(alkylene glycols), and glycols, and are used for forming the wall in a biological environment.

The expression, "drug formulation", as used herein, denotes any beneficial agent, compound or composition of matter, that can be delivered by the dispensing device to produce a beneficial and therapeutic results accompanied by a lessening in the incidence of mucosal irritation frequently associated with the drug. The drugs for the present purpose include any physiological or pharmacologically active substance that produces a local or systemic effect in animals, which latter term includes warm-blooded mammals, humans and primates, household, sport and farm animals, zoo animals, fishes and reptiles. The term, "physiologically" as used herein denotes the administration of a drug to produce normal levels and functions. The term, "pharmacologically" denotes variations in response to amounts of drug administered to the host. *Stedman's Medical Dictionary*, 1966, published by Williams and Wilkins, Baltimore, MD. The active drug that can be delivered include inorganic and organic drugs without limitations, drugs that act on the central nervous system, depressants, hypnotics, sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents, contraceptives, diuretics, sympathomimetics, anti-parasitics, neoplastics, hypoglycemics, ophthalmics, electrolytes, diagnostics, cardiovascular drugs, and the like.

The drugs administrable by the dispensing device of this invention in one present embodiment embrace drugs that irritate mucosal tissues, and whose adverse effects can be lessened, or eliminated by dispensing the drug according to the mode and manner of the invention.

Representative of these drugs include the non-steroidal anti-inflammatory inflammatory analgesic drugs. The non-steroidal anti-inflammatory analgesic drugs include a member selected from the group consisting of nonsteroidal propionic acid derivatives, nonsteroidal acetic acid derivatives, nonsteroidal fenamic acid derivatives, nonsteroidal biphenylcarboxylic acid derivatives, and nonsteroidal oxicam derivatives.

The propionic acid derivatives include a member selected from the group consisting of benoxaprofen, carprofen, flurbiprofen, fenoprofen, fenbufen, ibuprofen, indoprofen, ketoprofen, naproxen, miroprofen, oxaprozin, pranoprofen, pirprofen, suprofen, tiaprofenic acid, fluprofen, alminoprofen, bucloxic acid and the like. The acetic acid derivatives include a member selected from the group consisting of alcofenac acematacin, aspirin, diclofenac, indomethacin, ibufenac, isoxepac, furofenac, fentiazac, clidanac, oxpinac, sulindac, tolmetin, zomepirac, zidometracin, tenclofenac, tiopinac, and the like. The fenamic acid nonsteroid drugs include mefenamic acid, flufenamic acid, niflumic acid, meclofenamic acid, tolfenamic acid, and the like. Representative biphenylcarboxylic carboxylic acid nonsteroid drugs include diflunisol, flufenisol, and the like. Representative nonsteroidal oxicam drugs include isoxicam, piroxicam, sudoxicam, and the like. Other drugs include potassium chloride, potassium carbonate, and the like.

The dispensing device, optionally, can be used for dispensing drugs that are difficult to dispense in a rate controlled manner because they are poorly soluble or very soluble in aqueous fluids. These drugs can be dispensed by using the combined first and second hydrogel means of the invention. Representative drug that are poorly soluble in water include diphenidol, meclizine hydrochloride, prochlorperazine maleate, thiethylperazine maleate, anisindone, diphenadione, erthrityl tetranitrate, dizoxin, isofurophate, reserpine, acetazolamide, methazolamide, tolazamide, phenaglycodol, allopurinol, aluminum aspirin, and the like. Representative of drugs that are very soluble in water include prochlorperazine edisylate, ferrous sulfate, aminocaproic acid, mecamylamine hydrochloride, bethanechol chloride, methacholine chloride, methascopolamine bromide, tridihexethyl chloride, oxprenolol hydrochloride, and the like. The beneficial drugs are known to the art in *Pharmaceutical Sciences,* by Remington, 14th Ed., 1979, published by Mack Publishing Co., Easton, PA; *The Drug, The Nurse, The Patient, Including Current Drug Handbook,* 1974–76, by Falconer et al., published by Saunder Company, Philadelphia, PA; and *Medicinal Chemistry,* 3rd Ed. Vol. 1 and 2, by Burger, published by Wiley Interscience, New York.

The drug can be in various forms such as uncharged molecules, molecular complexes, pharmacologically acceptable salts such as hydrochloride, hydrobromide, sulfate, laurylate, palmitate, phosphate, nitrate, borate, acetate, maleate, tartrate, oleate, and salicylate. For acid drugs, salts of metals, amines, or organic cations, for example, quaternary ammonium can be used. Derivatives of drugs such as esters, ethers and amides can be used. Also, a drug that is water insoluble can be used in a form that is water soluble derivative thereof to serve as a solute, and on its release from the device is converted by enzymes, hydrolyzed by body pH, or other metabolic process, to the original biological active form.

The amount of drug present in the dispensing generally is an amount sufficient for performing a therapeutic program. Generally the dispensing device will contain from 0.05 ng to 7.5 g or more, with individual dispensing devices containing, for example, 25 ng, 1 mg, 25 mg, 50 mg, 125 mg, 250 mg, 500 mg, 750 mg, 1 g, 1.5 g, and the like. The dispensing device can be administered once, twice, thrice daily, or the like, over a prolonged period of one day to one year, or longer. The phrase, "drug formulation" as used for the purpose of this invention indicates the drug is present in the compartment with at least one hydrogel means. The phrase, "drug formulation" as used for the purpose of this invention denotes the drug is present in the compartment with at least one hydrogel means and, optionally, with at least one osmotically effective solute.

Osmotically effective solutes are known also as osmagents and osmotically effective compounds. The osmagent present in the device, when used according to the mode of the invention, are osmotically effective compounds soluble in fluid that enters the device, and exhibits an osmotic pressure gradient across the semipermeable wall against an exterior fluid. Osmotically effective osmagents useful for the present purpose include magnesium sulfate, magnesium chloride, sodium chloride, lithium chloride, potassium sulfate, sodium carbonate, sodium sulfate, lithium sulfate, sodium sulfate, mannitol, urea, sorbitol, inositol, raffinose, sucrose, glucose, glycose, and the like. The osmagent is usually present in an excess amount, and it can be in any physical form such as particle, powder, granule and the like. The osmotic pressure in atmosphere, ATM, of the osmagent suitable for the invention will be greater than zero ATM, generally from zero ATM up to 500 ATM, or higher. The amount of active osmagent in the compartment homogeneously or heterogeneously blended with the drug formulation and at least one hydrogel is usually from 0.01% to 40%, or higher. The osmotic pressure of an osmagent is measured in a commercially available osmometer that measures the vapor pressure difference between pure water and the solution to be analyzed and according to standard thermodynamic principles the vapor pressure ratio is converted into an osmotic pressure difference. The osmometer used for the present measurements is identified as Model 320B, Vapor Pressure Osmometer, manufactured by KNAUER, W. Germany and distributed by UTOPIA Instrument Co., Joliet, Ill. 60434.

The first hydrogel means and the second hydrogel carrier means suitable for the purpose of this invention comprise hydrogels that exhibit fluid absorbing or fluid imbibing properties. The hydrogel drug carrier means comprise hydrophilic, swellable polymers that interact with water and aqueous biological fluids and swell or expand to an equilibrium state. The hydrogels exhibit the ability to swell in aqueous fluids and retain a significant portion of the absorbed or imbibed fluid within the polymer structure. The hydrogels swell or expand to a very high degree, usually exhibiting a 2 fold volume increase, usually a 2 to 50 fold volume increase. Hydrogel compositions suitable for the present purpose comprise hydrogel compositions of plant, animal and synthetic origins. The hydrogens useful for forming the first hydrogel means are in a presently preferred embodiment neutral hydrogels. The phrase, "neutral hydrogel" as used herein denotes the hydrogel is substantially free of an electrical charge, and it is neither acidic or basic as defined in *Hackh's Chemical Dictionary*, 4th Ed., p 451, published in 1969 by McGraw Hill Book Co., NY. Representative neutral hydrogels comprise poly(hydroxyalkyl methacrylate) having a molecular weight of 20,000 to 5,000,000; poly(vinylpyrrolidone) having a molecular weight of about 10,000 to 360,000; poly(vinyl alcohol) having a low acetate content and lightly cross-linked with glyoxal, formaldehyde, glutaraldehyde and having a degree of polymerization from 200 to 30,000; poly(ethylene oxide) having a molecular weight from 10,000 to 5,000,000; starch graft copolymers comprising amylose and amylopectin and exhibiting a degree of polymerization from 200 to 10,000,000; cross-linked diester polyglucan having a degree of polymerization from 200 to 10,000,000; cellulose ethers having a degree of polymerization from 200 to 200,000 as exemplified by methylcellulose; hydroxyalkylalkylcellulose including ethylhydroxyethylcellulose, hydroxybutylmethylcellulose; hydroxyethylmethylcellulose and hydroxypropylmethylcellulose; neutral polysaccharides including nonionic compositions such as guar gum, locust bean and tamarind gum, and the like. The hydrogel polymers including hydrophilic hydrogels prepared from hydrophilic monomers such as monomethacrylates of polyethyleneglycols and monoethers, acrylamide and methacrylamide, N-substituted acrylamide and N-substituted methacrylamide, and the like.

The term, "ionic" as used herein denotes a polymeric hydrogel substituted with at least one chemical group that can dissociate into ions or become electrically charged in the presence of an aqueous type media. *Hackh's Chemical Dictionary*, 4th Ed., p 451, published in 1969, by McGraw-Hill Book Co., NY. Representative of ionic hydrogels are a member selected from the group consisting of anionic hydrogels, cationic hydrogels and polyelectrolyte hydrogels. Exemplary ionic hydrogels include carboxymethylcellulose; hydrogels formed of a copolymer of maleic anhydride with styrene, ethylene, propylene, butylene or isobutylene cross-linked with from 0.001 to about 0.5 moles of a polyunsaturated cross-linking agent per mole of maleic anhydride in the copolymer; hydrogels of N-vinyl lactams; acidic carboxy polymers known as carboxypolymethylene and carboxyvinylpolymers, a polymer consisting of acrylic acid cross-linked with polyallyl sucrose and sold under the trademark Carbopol®, acidic carboxy polymer having a molecular weight of 200,000 to 6,000,000, including sodium acidic carboxyvinyl hydrogel and potassium acidic carboxyvinyl hydrogel; Cyanamer® polyacrylamide; cross-linked indene-maleic anhydride polymers; Good-rite® polyacrylic acid polymer having a molecular weight of 60,000 to 500,000; ionic polysaccharides such as anionic carrageenin; anionic agar; anionic gum Arabic; anionic gum ghatti; and the like. Ionic hydrogels including hydrogels prepared from acidic monomers such as acrylic acid; methacrylic acid; crotonic acid; vinyl sulfonate; phosphorylated hydroxyalkylmethacrylates; basic monomers such as aminoalkylmethacrylate, and vinyl pyridine. The amount of a neutral hydrogel means in the device is about 1% to 60% and the amount of an ionic or anionic hydrogel carrier means in the device about 1% to 60%, with the total amount of both hydrogels when present about 1 to 70%, with the total amount of all ingredients present in the compartment of the device being 100%, such as 100 wt %. The representative polymers are known to the art in *Handbook of*

*Common Polymers*, by Scott and Roff, published by the Chemical Company, Cleveland, OH; *ACS Symposium Series*, No. 31, by Ratner & Hoffman, pp 1 to 36, 1976, published by the American Chemcial Society; and in *Recent Advances In Drug Delivery Systems*, by Schacht, pp 259–78, 1984, published by Plenum Press, NY.

The neutral hydrogel means generally will exhibit a viscosity of 1,500 centipoises to 10,000,000 centipoises when the dispensing device is in use at body animal temperature of 35° C. to 45° C. For polyethylene oxide with a molecular weight of 10,000 to 7,000,000, for a 2% solution, the viscosity is generally between 5 to 20,000 centipoises at a room temperature of 23° C.; for polyvinyl pyrrolidone with a molecular weight of between 10,000 to 500,000, for a 10% solution, the viscosity is generally between 5 to 5,000 centipoises at 25° C.; for hydroxypropylmethylcellulose having a molecular weight of between 1,000 to 200,000, a 2% solution in an aqueous media, the viscosity is from 10 centipoises to 2,000,000 centipoises. The ionic or anionic hydrogel carrier means in the device in the presence of a drug formulation and a neutral hydrogel will exhibit a viscosity up to 2,500 centipoises, and on its release from the device in the presence of fluid in an animal host, the viscosity will be greater than 2,500 centipoises. The viscosity of a drug solution, or the viscosity of a drug-viscosity hydrogel inducing solution is ascertained by conventional measurements. The viscosity of a solution can be measured with Wells-Brookfield Viscometer Model LVT, or with a Brookfield Viscometer. Methods and apparatus for measuring viscosity are known in *Pharmaceutical Science*, by Remington, 14th Ed., pp 359–71, 1970, published by Mack Publishing Co., Easton, PA.

The presence or the absence of irritation can be ascertained with known tests. One test for irritation consists in using rabbits that have been anesthetized, exposing the colon through a mid-line abdominal incision, having a segment distal to the caecum isolated by placing two ligatures 15 to 20 cm apart around the colon. The isolated segment is continuously supplied by its blood vessels and nerves. The isolated segment is clamped in a multi-chambered cell and each cell perfused with artificial intestinal fluid at 37° C. Delivery device dispensing a drug are placed in the cells directly into contact with the mucosa for a period of at least six hours. Tissue irritation in response to the test formulation was ascertained at the end of the test, leading to an irritation index. Procedures for measuring irritation are known in *J. Pharm. Sci.*, Vol. 60, No. 9, pp 1314–1316, 1971; *Arzneim-Forsch Drug Res.*, Vol. 23, No. 12, pp 1709–12, 1973; and in *Laryngoscope*, Vol. 93, pp 184–87, 1983.

The device of the invention is manufactured by standard techniques. For example, in one manufacture, the drug and other ingredients that may be housed in one area of the compartment adjacent to an exit passageway are pressed into a solid possessing dimensions that correspond to the internal dimensions of the area of the compartment the drug will occupy, or the drug and other ingredients and a solvent are mixed into a solid or semisolid form by conventional methods such as ball-milling, calendering, stirring, or rollmilling, and then pressed into a preselected shape. Next, a wall is applied around the compartment-forming, pressed reservoir drug hydrogel mass. The wall can be applied by molding, spraying or dipping the pressed shapes into a wall forming material. Another and presently preferred technique that can be used for applying the wall is the air suspension procedure. This procedure consists in suspending and tumbling the pressed drug hydrogel composition in a current of air and a wall forming composition until the wall is applied around the drug hydrogel composite. The air suspension procedure is described in U.S. Pat. No. 2,779,241; in *J. Am. Pharm. Assoc.*, Vol. 48, pp 451–59, 1979; *J. Am. Pharm. Assoc.*, Vol. 49, pp 82–84, 1960. Other standard manufacturing procedures are described in *Modern Plastics Encyclopedia*, Vol. 46, pp 62–70, 1969; and in *Pharmaceutical Sciences*, by Remington, 14th Ed., pp 1626–78, 1970, published by Mack Publishing Co., Easton, PA.

Exemplary solvents suitable for manufacturing the wall include inorganic and organic solvents that do not adversely harm the wall forming materials, and the final device. The solvents broadly include members selected from the group consisting of aqueous solvents, alcohols, ketones, esters, ethers, aliphatic hydrocarbons, halogenated solvents, cycloaliphatic, aromatics, heterocyclic solvents, and mixtures thereof. Typical solvents include acetone, diacetone, alcohol, methanol, ethanol, isopropyl alcohol, butyl alcohol, methyl acetate, ethyl acetate, isopropyl acetate, n-butyl acetate, methyl isopropyl ketone, methylpropyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, water, and mixtures thereof such as acetone and ethyl alcohol, methylene dichloride and methanol, ethylene dichloride and methanol, and the like.

The expression "exit means" as used herein comprises means and methods suitable for releasing a beneficial drug from the dispensing device. The means include at least one passageway or orifice that passes through the wall for communicating with the drug in the compartment. The expression, "at least one passageway" includes aperture, orifice, bore, pore, porous element through which a beneficial drug can migrate, a hollow fiber, capillary tube, and the like. The expression also includes a material that erodes or is leached from the wall in the fluid environment of use to produce at least one passageway in the device. Representative materials suitable for forming at least one passageway, or a multiplicity of passageways, include an erodible poly(glycolic) or poly(lactic) acid member in the wall, gelatinous filaments, poly(vinyl alcohol), leachable materials such as fluid removable pore former polysaccharide salt, oxide and the like. A passageway or a plurality of passageways can be formed by leaching a material such as sorbitol from the wall. The passageway can have any shape. For example, round, triangular, square, elliptical, irregular, and the like. Also, the device can be constructed with one or more passageways. In an embodiment, when the device is fabricated with more than one passageway, the passageway can be construed as the functional equivalent in an operative embodiment of a single osmotic passageway. The expression, "osmotic passageway" includes passageways formed by mechanical drilling, laser drilling, eroding or leaching a passageway through the wall. Generally, for the purpose of this invention, an osmotic passageway will have a maximum cross-sectional area, $A_{max}$, defined by relation (5):

$$A_{max} = \frac{L}{F} \times \frac{M}{t} \times \frac{1}{DS} \qquad (5)$$

wherein L is the length of the passageway, (M/t) is the mass delivery rate of the agent released per unit of time, D is the diffusion coefficient of the medicine in the release solution, S is the solubility of the medicine in the fluid and F has a value of approximately 2 to 1000, said osmotic passageway having a minimum area, $A_{min}$, defined by relation (6):

$$A_{min} = \left[ \frac{Lv}{t} \times 8 \times \frac{\pi \eta}{\Delta P} \right]^{\frac{1}{2}} \qquad (6)$$

wherein L is the length of the passageway, v/t is the volume of the medicine released per unit of time, $\pi$ is 3.14, $\eta$ is the viscosity of the solution being released, and $\Delta P$ is the hydrostatic pressure difference between the inside and the outside of the compartment and having a value up to 20 ATM. The dimension for the osmotic passageway is disclosed in U.S. Pat. No. 3,916,899. Laser drilling equipment having photo detection means for orienting a device for surface selected drilling is known in U.S. Pat. Nos. 4,063,064; 4,088,864, and by leaching in U.S. Pat. No. 4,200,098.

DESCRIPTION OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

A drug dispensing device is manufactured for dispensing the beneficial drug potassium chloride to a gastrointestinal tract as follows: first, a compartment forming composition comprising, in weight percent, 92.25% potassium chloride powder, 5% potassium carboxypolymethylene, 2% polyethylene oxide having a molecular weight of about 5,000,000, and 0.5% silicon dioxide are mixed together. Next, the mixture is passed through a 40 mesh stainless steel screen and then dry blended in a V-blender for 30 minutes to produce a uniform blend. Next, 0.25% magnesium stearate is passed through an 80 mesh stainless steel screen, and the blend given an additional 5 to 8 minutes blend.

Then, the homogeneously dry blended powder is placed into a hopper and fed to a compartment forming press, and known amounts of the blend compressed into ⅜ inch oval shapes designed for oral use. The oval shaped precompartments are coated next in a Accela-Cota® wall forming coater with a wall forming composition comprising 91% cellulose acetate having an acetyl content of 39.8% and 9% polyethylene glycol 3350. After coating, the wall coated drug compartments are removed from the coater and transferred to a drying oven for removing the residual organic solvent used during the wall forming procedure. Next, the coated devices are transferred to a 50° C. forced air oven for drying about 12 hours. Then, passageways are formed in the wall of the device using a laser for drilling two passageways on the major axis of each face of the dispensing device.

EXAMPLES 2-6

The procedure of Example 1 is repeated in the following examples with all manufacturing procedures as described for providing the following dispensing devices:

2. A dispensing device comprising a compartment weighing 824.18 mg comprising 91% powdered potassium chloride, 5% potassium carboxypolymethylene, 3% polyethylene oxide coagulant, 0.5% magnesium stearate, and 0.5% silica, a wall weighing 38.50 mg comprising 91% cellulose acetate 39.8% acetyl and 9% polyethylene glycol 3350. The device had 2 passageways with a diameter of 0.51 mm. The device had an average release rate of 29 mg per hour and a cumulative amount released of 710 mg in 24 hours.

3. A dispensing device comprising a compartment weighing 815.22 mg comprising 92% powdered potassium chloride, 5% potassium carboxypolymethylene, 2% polyethylene oxide having a molecular weight of 5,000,000, 0.5% magnesium stearate, 0.5% silica, a wall weighing 39.30 mg comprising 91% cellulose acetate having an acetyl content of 39.8% and 9.0% polyethylene glycol. The device has two passageways with a diameter of 0.5 mm. The device exhibits an average release rate of 30 mg per hour for 24 hours with a cumulative amount released of 718.8 mgs.

4. A dispensing device comprising a compartment weighing 838 mg comprising 89.5% potassium chloride powder, 7.2% potassium carboxyvinyl polymer, 2.8% polyethylene oxide coagulant having a molecular weight of 5,000,000, 0.25% silica and 0.25% magnesium stearate, and a wall weighing 21.03 mg comprising 97% cellulose acetate 39.8% and 3% polyethylene glycol. The device had two passageways with a diameter of 0.51 mm. The device had an average release rate of 29 mg per hour for 24 hours and a cumulative amount released of 698 mgs.

5. A dispensing device comprising a compartment weighing 872 mg comprising 86% potassium chloride, 10% sodium Carbopol 934 P a carboxyvinyl polymer of acrylic acid crosslinked with polyallyl ether of sucrose having an average of about 5.8 allyl groups for each molecule of sucrose, and 4% Polyox® coagulant a hydrophilic polymer of polyethylene oxide having a molecular weight of about 5,000,000, and a wall having a weight of 18.6 mg comprising 97% cellulose acetate 39.8 and 3% polyethylene glycol 4000. The device had two passageways with a diameter of 0.508 mm. The device had an average rate of release of 29.7 mg per hour and a cumulative amount release of 716 mg in 24 hours.

6. A dispensing device comprising a compartment weighing 872 mg comprising 86% potassium chloride, 10% methoxycellulose and 4% Polyox® coagulant, and a wall weighing 18.5 mg comprising 95% cellulose acetate 39.8% and 5% polyethylene glycol 4000. The dispenser at two passageways with a diameter of 0.51 mm. The device had an average rate of release of 30.5 mg per hour and a cumulative amount released of 731.4 mg over an extended period of 24 hours.

EXAMPLE 7

An osmotic therapeutic device for the controlled and the continuous oral delivery of the beneficial drug potassium chloride is prepared according to the above procedure. The device of this example comprises a compartment containing potassium chloride powder 750 mg, potassium Carbomer ® 40.65 mg, a potassium carboxypolymethylene hydrogel with a molecular weight of about 300,000, polyethylene oxide coagulant 16.3 mg, a hydrogel having a molecular weight of about 5,000,000, silicon dioxide 4 mg and magnesium stearate 2 mg. The device comprises a 4 mil thick wall of cellulose acetate 91% and polyethylene glycol 9%. The device comprises 4 passageways of 20 mil diameter and exhibited at 90 of 20 hrs. The device collapes at the end of the drug delivery period thereby enhancing passage of the device from the gastrointestinal tract. The device collapses under a pressure of 40 mm Hg to 270 mm Hg. The device collapses when the external pressure exerted against the device exceeds both the resistance exerted by the wall of the device and the resistance generated by viscous flow of the drug gel composition hydrodynamically pumped through the passageway of the device. Hence, the collapse pressure $P_c$ is expressed as two components:

$$P_c = P_h + P_G \quad (7)$$

wherein $P_h$ is the pressure required to collapse the empty device and $p_G$ is the pressure required to deliver the contents of the device from the device. The factor $P_h$ can further be expressed as equation (8):

$$P_h \approx 0.8 \frac{Eh^2}{R^2} \quad (8)$$

where E is Young's modulus of the wall, h is the thickness of the wall and R is the maximum radius of curvature of the device. The pressure required to deliver a viscous drug gel composition through the passageway, $P_G$, is composed of two pressure terms as expressed by equation (9):

$$P_G = \Delta P_{entrance} + \Delta P_{capillary} \quad (9)$$

where $\Delta P_{entrance}$ is the pressure drop of the viscous composition entering the passageway and $\Delta P_{capillary}$ is the pressure drop of the composition flowing through the passageway. According to Poiseuille law, the laminar viscous flow through a capillary is expressed by equation (10):

$$\Delta P_{capillary} = \eta Q \left( \frac{8h}{\pi r^4} \right) \quad (10)$$

where $\eta$ is the viscosity of the composition inside the device, h is the thickness of the wall, r is the radius of the passageway, and Q is the volume flow rate through the passageway. For a small Reynold's number, the entrance effect can be approximated by a tube length of L equal to 2 r, as expressed by equation (11):

$$P_G = \eta Q \left( \frac{8}{\pi r^4} \right) (h + 2r) \quad (11)$$

Substituting (8) and (11) into (7) results in equation (12):

$$P_c = 0.8 \frac{Eh^2}{R^2} + \eta Q \left( \frac{8}{\pi r^4} \right) (h + 2r) \quad (12)$$

Thus, for a device comprising potassium chloride the collapse pressure is calculated as follows: $E=1.4(10)^5$ psi for a cellulose acetate wall having a thickness h of 1.7 mil and R of 0.5 inch, (about 13 mm), the $P_h$ is given by equation (13) and (14):

$$P_h = 0.8 \frac{(1.4 \times 10^5)(0.0017)^2}{(0.5^2)} \quad (13)$$

$$P_h = 1.3 \text{ psi} = 67 \text{ mm } H_g \quad (14)$$

Therefore, from equation (12), the $P_c$ is as follows (15):

$$P_c = 67 + \eta Q \left( \frac{8}{\pi r^4} \right) (h + 2r) \quad (15)$$

where r=10 mil, (0.026 cm), Q=0.43 ml/min assuming all the contents are compressed out in about 1 min, $\eta$ is the viscosity of the core solution as set forth in FIG. 15, for a final $P_c$ equal to 67+0.0043 n for the device, having 4 passageways for delivering the drug over time.

EXAMPLE 8

An osmotic therapeutic device for the controlled and continuous delivery of indomethacin sodium trihydrate orally to the gastrointestinal tract is prepared as follows: a drug composition is prepared for housing in the compartment of the device by thoroughly blending 325 mg of sodium indomethacin trihydrate, 100 mg of sodium carboxypolymethylene, 25 mg of methoxycellulose, 25 mg of polyethylene oxide, 3 mg silica and 2 mg of magnesium stearate and then pressed in a Manesty press with a 7/16 inch punch using a pressure head of 1½ tons to produce the drug hydrogel composition.

Next, a semipermeable wall is formed by blending 170 g of cellulose acetate having an acetyl content of 39.8 with 2325 ml of methylene chloride and 1992 mil of methanol, and spray coating the drug hydrogel composition in an air suspension machine until a 2.1 ml thick semipermeable wall surrounds the compartment. The coated device is dried for 72 hours at 50° C., and then three 15 mil (0.34 mm) passageways are laseer drilled through the wall for releasing the beneficial drug over an extended period of time.

EXAMPLE 9

A device is manufactured in the form of an oral delivery device for delivering the beneficial analgesic sodium salicylate to the gastrointestinal tract is manufactured as follows: first a composition comprising 325 mg sodium salicylate 18 mg of sodium carboxypolymethylene, 11 mg of polyacrylamide, 10 mg of magnesium stearate and 10 mg of silica is prepared by blending the ingredients into a homogeneous blend and then pressing the blend into a solid mass. The blend is compressed in a Manesty tableting machine set to a Stoke's hardness of 8 kg. Next, the compressed mass is coated by dipping approximately one-half of the device into a wall forming composition comprising 45% by weight of cellulose acetate having an acetyl content of 39.8%, 45% by weight of sorbitol and 10% by weight of polyethylene glycol. The coating is applied from a coating composition comprising methylene chloride-methanol-water, 62:35:3 by weight. The sorbitol is leached from the wall during operation to form in situ passageways of controlled release porosity. Next, the remainder of the composition is coated with a semipermeable wall forming composition by dipping the previously uncoated area into a composition comprising 50% by weight of cellulose acetate having an acetyl content of 39.8% and 50% by weight of cellulose acetate having an acetyl content of 32%. The latter wall forming composition is applied from a solvent consisting of methylene chloride and methanol 80:20 by weight. The device delivers the drug through the in situ passageways as a controlled rate over time.

EXAMPLE 10

The procedure described in Example 9 is repeated with all the conditions as set forth, except that in this example the beneficial drug is the sodium salt of naproxen.

The present invention's unexpected ability to lessen unwanted side effects associated with the administration of many drugs is demonstrated by using the irritation test. This test, mentioned above, demonstrates the effect of drug contact on mucosal tissue. The test measures the irritation area in cm$^2$, the irritation score, and the irritation index. The unexpected result indicates a lessening of the incidence of irritation is evident from a low irritation index. A comparison of the effects of the drug potassium chloride administered by various procedures is set forth below. An osmotic device administering potassium chloride free of hydrogel exhibited an irritation area of 6.7 cm$^2$, an irritation score of 3.5 and irritation index of 23.5. Potassium chloride administered by leaching from a microporous polymer exhibited an irritation area of 4.1 cm$^2$, an irritation score of 3.5 and an irritation index of 14.4. An osmotic device administering a composition comprising potassium chloride and 30% polyethylene oxide having a molecular weight of 600,000 exhibited an irritation area of 4.0 cm, an irritation score of 3.5 and an irritation index of 14.1. An osmotic device administering a composition comprising potassium chloride and 30% starch graft polymer exhibited an irritation area of 3.2 cm$^2$, an irritation score of 3.5 and an irritation index of 11.0. An osmotic device administering a composition comprising potassium chloride and 30% carboxyvinyl polymer having a molecular weight of 200,000 exhibited an irritation area of 2.0 cm$^2$, an irritation score of 3.3 and an irritation index of 6.6. An osmotic device administering a composition comprising potassium chloride, 5% potassium carboxypolymethylene having a molecular weight of 3,000,000 and 2% polyethylene oxide having a molecular weight of 5,000,000 exhibited an irritation area of 0.4 cm$^2$, an irritation score of 1 and an irritation index less than 1. The osmotic Device used in the test had a $t_{90}$ of 12 hrs and a delivery rate of 45 mg/hr for potassium chloride.

In summary, it will be readily appreciated that the present invention contributes to the art an unobvious drug delivery device possessing wide and practical application. While the invention has been described and pointed out in detail and with reference to operative embodiments thereof, it will be understood that those skilled in the art will appreciate that various changes, modifications, substitutions and omissions can be made without departing from the spirit of the invention. It is intended, therefore, that the invention embrace those equivalents within the scope of the claims which follow:

We claim:

1. A process for lessening the incidence of irritation of a mucosal environment associated with the beneficial drug potassium chloride that produces irritation of a mucosal environment, said process comprising the steps of administering a composition comprising polyethylene oxide, potassium carboxyvinyl polymer and potassium chloride to a mucosal environment, lessening the incidence of unwanted irritation by the polyethylene oxide and potassium carboxyvinyl polymer cooperating in the presence of fluid in the mucosal environment reduce direct contact of the potassium chloride within the mucosal tissue, thereby lessening the incidence of irritation associated with potassium chloride therapy.

2. A process for lessening the incidence of irritation of a mucosal environment associated with a drug that produces irritation of a mucosal environment, said process comprising administering a composition comprising means for lessening the incidence of irritation associated with a drug that produces irritation on contact, said means comprising (a) a first hydrogel that is essentially neutral in fluid in the mucosal environment which first hydrogel interacts with the fluid and swells, and (b) a second hydrogel that is ionic in fluid in the mucosal environment which second hydrogel interacts with the fluid and swells to a lesser volume than the first hydrogel, and which process lessens the incidence of irritation by the first hydrogel and second hydrogel acting together in the mucosal environment to lessen the incidence of irritation of the mucosal tissue associated with the drug.

* * * * *